United States Patent
Chung et al.

(10) Patent No.: US 12,310,869 B2
(45) Date of Patent: May 27, 2025

(54) STEERING WIRE ATTACH FOR ANGULATION

(71) Applicant: W. L. Gore & Associates, Inc., Newark, DE (US)

(72) Inventors: Karl R. Chung, Phoenix, AZ (US); Matthew S. Beard, Phoenix, AZ (US); Martin J. Sector, Gilbert, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1311 days.

(21) Appl. No.: 16/562,669

(22) Filed: Sep. 6, 2019

(65) Prior Publication Data

US 2019/0388256 A1    Dec. 26, 2019

Related U.S. Application Data

(63) Continuation of application No. PCT/US2018/021442, filed on Mar. 8, 2018.

(60) Provisional application No. 62/468,618, filed on Mar. 8, 2017.

(51) Int. Cl.
*A61F 2/95* (2013.01)
*A61F 2/07* (2013.01)
*A61F 2/06* (2013.01)
*A61M 25/01* (2006.01)

(52) U.S. Cl.
CPC .................. *A61F 2/95* (2013.01); *A61F 2/07* (2013.01); *A61F 2002/065* (2013.01); *A61F 2002/9511* (2013.01); *A61M 2025/015* (2013.01)

(58) Field of Classification Search
CPC .................... A61F 2/9522; A61F 2/954; A61F 2002/9505; A61F 2002/9511
See application file for complete search history.

(56) References Cited

U.S. PATENT DOCUMENTS

| | | |
|---|---|---|
| 1,355,373 A | 10/1920 | Dell |
| 1,506,432 A | 8/1924 | Kimmel |
| 1,851,314 A | 3/1932 | Knoche |
| 3,625,451 A | 12/1971 | Anderson |
| 3,915,167 A | 10/1975 | Waterman |
| 3,953,566 A | 4/1976 | Gore |
| 4,187,390 A | 2/1980 | Gore |
| 4,503,569 A | 3/1985 | Dotter |
| 4,512,338 A | 4/1985 | Balko et al. |

(Continued)

FOREIGN PATENT DOCUMENTS

| | | |
|---|---|---|
| CN | 101554343 A | 10/2009 |
| CN | 101780306 A | 7/2010 |

(Continued)

OTHER PUBLICATIONS

International Preliminary Report on Patentability received for PCT Patent Application No. PCT/US2018/049053, mailed on Mar. 11, 2021, 8 pages.

(Continued)

*Primary Examiner* — Martin T Ton

(57) ABSTRACT

Various aspects of the present disclosure are directed toward apparatuses, systems, and methods for example device delivery. The apparatuses, systems, and methods may include an actuation wire coupled to the expandable device at one or more locations thereon, the actuation wire being configured to steer the expandable device during delivery.

17 Claims, 10 Drawing Sheets

(56) References Cited

U.S. PATENT DOCUMENTS

| | | | |
|---|---|---|---|
| 4,655,246 A | 4/1987 | Phlipot et al. | |
| 4,858,810 A | 8/1989 | Intlekofer et al. | |
| 4,990,155 A | 2/1991 | Wilkoff | |
| 5,035,706 A | 7/1991 | Giantureo et al. | |
| 5,037,427 A | 8/1991 | Harada et al. | |
| 5,147,370 A | 9/1992 | McNamara et al. | |
| 5,211,658 A | 5/1993 | Clouse | |
| 5,217,486 A | 6/1993 | Rice et al. | |
| 5,221,261 A | 6/1993 | Termin et al. | |
| 5,276,276 A | 1/1994 | Gunn | |
| 5,325,746 A | 7/1994 | Anderson | |
| 5,344,427 A | 9/1994 | Cottenceau et al. | |
| 5,491,704 A | 2/1996 | Duron | |
| 5,527,338 A | 6/1996 | Purdy | |
| 5,554,183 A * | 9/1996 | Nazari | A61F 2/95 623/1.13 |
| 5,562,726 A | 10/1996 | Chuter | |
| 5,577,299 A | 11/1996 | Thompson et al. | |
| 5,693,083 A | 12/1997 | Baker et al. | |
| 5,707,376 A | 1/1998 | Kavteladze et al. | |
| 5,709,704 A | 1/1998 | Nott et al. | |
| 5,713,917 A | 2/1998 | Leonhardt et al. | |
| 5,713,948 A | 2/1998 | Uflacker | |
| 5,720,776 A | 2/1998 | Chuter et al. | |
| 5,725,552 A | 3/1998 | Kotula et al. | |
| 5,776,141 A | 7/1998 | Klein et al. | |
| 5,776,186 A | 7/1998 | Uflacker | |
| 5,782,909 A | 7/1998 | Quiachon et al. | |
| 5,843,162 A | 12/1998 | Inoue | |
| 5,873,906 A | 2/1999 | Lau et al. | |
| 5,904,703 A | 5/1999 | Gilson | |
| 5,961,546 A | 10/1999 | Robinson et al. | |
| 6,013,093 A | 1/2000 | Nott et al. | |
| 6,015,431 A | 1/2000 | Thornton et al. | |
| 6,019,785 A | 2/2000 | Strecker | |
| 6,042,588 A | 3/2000 | Munsinger et al. | |
| 6,042,602 A | 3/2000 | Wells | |
| 6,143,021 A | 11/2000 | Staehle | |
| 6,152,144 A | 11/2000 | Lesh et al. | |
| 6,165,195 A | 12/2000 | Wilson | |
| 6,203,550 B1 | 3/2001 | Olson | |
| 6,214,025 B1 | 4/2001 | Thistle et al. | |
| 6,224,627 B1 | 5/2001 | Armstrong et al. | |
| 6,231,561 B1 | 5/2001 | Frazier et al. | |
| 6,231,581 B1 | 5/2001 | Shank et al. | |
| 6,231,589 B1 | 5/2001 | Wessman et al. | |
| 6,264,671 B1 | 7/2001 | Stack et al. | |
| 6,273,900 B1 | 8/2001 | Nott et al. | |
| 6,302,891 B1 | 10/2001 | Nadal | |
| 6,312,454 B1 | 11/2001 | Stoeckel et al. | |
| 6,322,585 B1 | 11/2001 | Khosravi et al. | |
| 6,328,727 B1 | 12/2001 | Frazier et al. | |
| 6,346,117 B1 | 2/2002 | Greenhalgh | |
| 6,352,561 B1 | 3/2002 | Leopold et al. | |
| 6,451,051 B2 | 9/2002 | Drasler et al. | |
| 6,475,234 B1 | 11/2002 | Richter et al. | |
| 6,485,513 B1 | 11/2002 | Fan | |
| 6,491,704 B2 | 12/2002 | Gifford et al. | |
| 6,524,335 B1 | 2/2003 | Hartley et al. | |
| 6,527,779 B1 | 3/2003 | Rourke | |
| 6,551,303 B1 | 4/2003 | Van et al. | |
| 6,551,350 B1 | 4/2003 | Thornton et al. | |
| 6,572,643 B1 | 6/2003 | Gharibadeh | |
| 6,572,646 B1 | 6/2003 | Boylan et al. | |
| 6,689,150 B1 | 2/2004 | Vantassel et al. | |
| 6,705,563 B2 | 3/2004 | Luo et al. | |
| 6,712,836 B1 | 3/2004 | Berg et al. | |
| 6,712,842 B1 | 3/2004 | Gifford et al. | |
| 6,730,108 B2 | 5/2004 | Van et al. | |
| 6,733,521 B2 | 5/2004 | Chobotov et al. | |
| 6,743,210 B2 | 6/2004 | Hart et al. | |
| 6,746,472 B2 | 6/2004 | Frazier et al. | |
| 6,755,854 B2 | 6/2004 | Gillick et al. | |
| 6,827,731 B2 | 12/2004 | Armstrong et al. | |
| 6,866,669 B2 | 3/2005 | Buzzard et al. | |
| 6,884,259 B2 | 4/2005 | Tran et al. | |
| 6,911,039 B2 | 6/2005 | Shiu et al. | |
| 6,926,732 B2 | 8/2005 | Derus et al. | |
| 6,939,352 B2 | 9/2005 | Buzzard et al. | |
| 6,945,990 B2 | 9/2005 | Greenan | |
| 6,949,113 B2 | 9/2005 | Van et al. | |
| 6,974,471 B2 | 12/2005 | Van et al. | |
| 6,994,092 B2 | 2/2006 | Van et al. | |
| 7,033,368 B2 | 4/2006 | Rourke | |
| 7,044,134 B2 | 5/2006 | Khairkhahan et al. | |
| 7,049,380 B1 | 5/2006 | Chang et al. | |
| 7,052,511 B2 | 5/2006 | Weldon et al. | |
| 7,066,951 B2 | 6/2006 | Chobotov | |
| 7,081,132 B2 | 7/2006 | Cook et al. | |
| 7,122,050 B2 | 10/2006 | Randall et al. | |
| 7,128,073 B1 | 10/2006 | Van et al. | |
| 7,147,657 B2 | 12/2006 | Chiang et al. | |
| 7,147,661 B2 | 12/2006 | Chobotov et al. | |
| 7,169,160 B1 | 1/2007 | Middleman et al. | |
| 7,198,636 B2 | 4/2007 | Cully et al. | |
| 7,208,003 B2 | 4/2007 | Davis et al. | |
| 7,252,680 B2 | 8/2007 | Freitag | |
| 7,331,992 B2 | 2/2008 | Randall et al. | |
| 7,396,359 B1 | 7/2008 | Derowe et al. | |
| 7,419,498 B2 | 9/2008 | Opolski et al. | |
| 7,462,675 B2 | 12/2008 | Chang et al. | |
| 7,555,034 B2 | 6/2009 | Shin et al. | |
| 7,566,336 B2 | 7/2009 | Corcoran et al. | |
| 7,572,289 B2 | 8/2009 | Sisken et al. | |
| 7,601,159 B2 | 10/2009 | Ewers et al. | |
| 7,611,528 B2 | 11/2009 | Goodson et al. | |
| 7,655,034 B2 | 2/2010 | Mitchell et al. | |
| 7,771,455 B2 | 8/2010 | Ken | |
| 7,815,591 B2 | 10/2010 | Levine et al. | |
| 7,837,724 B2 | 11/2010 | Keeble et al. | |
| 7,846,179 B2 | 12/2010 | Belef et al. | |
| 7,887,580 B2 | 2/2011 | Randall et al. | |
| 7,938,851 B2 | 5/2011 | Olson et al. | |
| 7,976,575 B2 | 7/2011 | Hartley | |
| 7,998,189 B2 | 8/2011 | Koelbel et al. | |
| 8,029,559 B2 | 10/2011 | Sisken et al. | |
| 8,043,356 B2 | 10/2011 | Koelbel et al. | |
| 8,048,440 B2 | 11/2011 | Chang et al. | |
| 8,062,349 B2 | 11/2011 | Moore et al. | |
| 8,080,032 B2 | 12/2011 | Van et al. | |
| 8,167,927 B2 | 5/2012 | Chobotov | |
| 8,231,650 B2 | 7/2012 | Cully et al. | |
| 8,241,346 B2 | 8/2012 | Chobotov | |
| 8,241,350 B2 | 8/2012 | Randall et al. | |
| 8,252,037 B2 | 8/2012 | Styrc et al. | |
| 8,257,431 B2 | 9/2012 | Henderson et al. | |
| 8,262,671 B2 | 9/2012 | Osypka | |
| 8,273,105 B2 | 9/2012 | Cohen et al. | |
| 8,287,583 B2 | 10/2012 | Laduca et al. | |
| 8,328,861 B2 | 12/2012 | Martin et al. | |
| 8,361,135 B2 | 1/2013 | Dittman | |
| 8,394,139 B2 | 3/2013 | Roeder et al. | |
| 8,424,166 B2 | 4/2013 | Dorneman et al. | |
| 8,449,595 B2 | 5/2013 | Ouellette et al. | |
| 8,469,990 B2 | 6/2013 | McGuckin et al. | |
| 8,480,725 B2 | 7/2013 | Rasmussen et al. | |
| 8,523,897 B2 | 9/2013 | Van et al. | |
| 8,529,597 B2 | 9/2013 | Linder et al. | |
| 8,685,055 B2 | 4/2014 | Vantassel et al. | |
| 8,690,911 B2 | 4/2014 | Miles et al. | |
| 8,834,519 B2 | 9/2014 | Van et al. | |
| 8,870,947 B2 | 10/2014 | Shaw | |
| 8,968,384 B2 | 3/2015 | Pearson et al. | |
| 8,979,919 B2 | 3/2015 | Goddard et al. | |
| 8,986,363 B2 | 3/2015 | McHugo et al. | |
| 9,060,895 B2 | 6/2015 | Hartley et al. | |
| 9,095,466 B2 | 8/2015 | Norris et al. | |
| 9,132,025 B2 | 9/2015 | Aristizabal et al. | |
| 9,254,204 B2 | 2/2016 | Roeder et al. | |
| 9,265,596 B2 | 2/2016 | Shank et al. | |
| 9,308,349 B2 | 4/2016 | Rezac et al. | |
| 9,351,858 B2 | 5/2016 | Chobotov et al. | |
| 9,364,359 B2 | 6/2016 | Crawford et al. | |
| 9,375,308 B2 | 6/2016 | Norris | |

(56) References Cited

U.S. PATENT DOCUMENTS

| | | |
|---|---|---|
| 9,387,097 B2 | 7/2016 | Eblacas et al. |
| 9,498,361 B2 | 11/2016 | Roeder et al. |
| 9,585,743 B2 | 3/2017 | Cartledge et al. |
| 9,585,774 B2 | 3/2017 | Aristizabal et al. |
| 9,681,968 B2 | 6/2017 | Goetz et al. |
| 9,700,701 B2 | 7/2017 | Benjamin et al. |
| 9,730,700 B2 | 8/2017 | Herbowy et al. |
| 9,770,322 B2 | 9/2017 | Burkart et al. |
| 9,782,282 B2 | 10/2017 | Bloss et al. |
| 9,782,284 B2 | 10/2017 | Hartley et al. |
| 9,877,858 B2 | 1/2018 | Beard et al. |
| 9,937,070 B2 | 4/2018 | Skelton et al. |
| 9,987,155 B1 | 6/2018 | Sondreaal |
| 11,123,174 B2 | 9/2021 | Burkart et al. |
| 11,324,615 B2 | 5/2022 | Bloss et al. |
| 11,382,781 B2 | 7/2022 | Sector et al. |
| 2001/0034549 A1 | 10/2001 | Bartholf et al. |
| 2001/0037142 A1 | 11/2001 | Stelter et al. |
| 2002/0007208 A1 | 1/2002 | Strecker |
| 2002/0029076 A1 | 3/2002 | Yee |
| 2002/0029077 A1 | 3/2002 | Leopold et al. |
| 2002/0040236 A1 | 4/2002 | Lau et al. |
| 2002/0091439 A1 | 7/2002 | Baker et al. |
| 2002/0099431 A1 | 7/2002 | Armstrong et al. |
| 2002/0151953 A1 | 10/2002 | Chobotov et al. |
| 2003/0088305 A1 | 5/2003 | Van et al. |
| 2003/0098383 A1 | 5/2003 | Luo et al. |
| 2003/0149467 A1 | 8/2003 | Linder et al. |
| 2003/0181942 A1 | 9/2003 | Sutton et al. |
| 2004/0034366 A1 | 2/2004 | Van et al. |
| 2004/0054396 A1 | 3/2004 | Hartley et al. |
| 2004/0063805 A1 | 4/2004 | Pacetti et al. |
| 2004/0073289 A1 | 4/2004 | Hartley |
| 2004/0122503 A1 | 6/2004 | Campbell et al. |
| 2004/0138734 A1 | 7/2004 | Chobotov et al. |
| 2004/0143315 A1 | 7/2004 | Bruun et al. |
| 2005/0038470 A1 | 2/2005 | Van et al. |
| 2005/0049667 A1 | 3/2005 | Arbefeuille et al. |
| 2005/0070820 A1 | 3/2005 | Boutillette et al. |
| 2005/0080476 A1 | 4/2005 | Gunderson et al. |
| 2005/0085890 A1 | 4/2005 | Rasmussen et al. |
| 2005/0125031 A1 | 6/2005 | Pipenhagen et al. |
| 2005/0240257 A1 | 10/2005 | Ishimaru et al. |
| 2006/0004433 A1 | 1/2006 | Greenberg et al. |
| 2006/0015171 A1 | 1/2006 | Armstrong |
| 2006/0058833 A1 | 3/2006 | Vancamp et al. |
| 2006/0155366 A1 | 7/2006 | Laduca et al. |
| 2006/0198866 A1 | 9/2006 | Chang et al. |
| 2006/0254569 A1 | 11/2006 | Chipman |
| 2006/0264980 A1 | 11/2006 | Khairkhahan et al. |
| 2007/0016281 A1 | 1/2007 | Melsheimer |
| 2007/0066993 A1 | 3/2007 | Kreidler |
| 2007/0088424 A1 | 4/2007 | Greenberg et al. |
| 2007/0100427 A1 | 5/2007 | Perouse |
| 2007/0162048 A1 | 7/2007 | Quinn et al. |
| 2007/0167955 A1 | 7/2007 | Arnault et al. |
| 2007/0198077 A1 | 8/2007 | Cully et al. |
| 2007/0198078 A1 | 8/2007 | Berra et al. |
| 2007/0219467 A1 | 9/2007 | Clark et al. |
| 2007/0225797 A1 | 9/2007 | Krivoruhko |
| 2007/0248640 A1 | 10/2007 | Karabey et al. |
| 2007/0249980 A1 | 10/2007 | Carrez et al. |
| 2007/0255390 A1 | 11/2007 | Ducke et al. |
| 2007/0270891 A1 | 11/2007 | McGuckin, Jr. |
| 2008/0027529 A1 | 1/2008 | Hartley et al. |
| 2008/0039925 A1 | 2/2008 | Ishimaru et al. |
| 2008/0114440 A1 | 5/2008 | Hlavka et al. |
| 2008/0147111 A1 | 6/2008 | Johnson et al. |
| 2008/0178434 A1 | 7/2008 | Bulanda |
| 2008/0208329 A1 | 8/2008 | Bishop et al. |
| 2008/0269785 A1 | 10/2008 | Lampropoulos et al. |
| 2008/0294234 A1 | 11/2008 | Hartley et al. |
| 2009/0048656 A1 | 2/2009 | Wen |
| 2009/0054723 A1 | 2/2009 | Khairkhahan et al. |
| 2009/0062838 A1 | 3/2009 | Brumleve et al. |
| 2009/0082844 A1 | 3/2009 | Zacharias et al. |
| 2009/0099596 A1 | 4/2009 | McGuckin et al. |
| 2009/0099640 A1 | 4/2009 | Weng |
| 2009/0112249 A1 | 4/2009 | Miles et al. |
| 2009/0171386 A1 | 7/2009 | Amplatz et al. |
| 2009/0182407 A1* | 7/2009 | Leanna ............... A61F 2/9525 623/1.11 |
| 2009/0182411 A1 | 7/2009 | Irwin et al. |
| 2009/0204198 A1 | 8/2009 | Jensen et al. |
| 2009/0216308 A1* | 8/2009 | Hartley ............... A61F 2/95 623/1.11 |
| 2009/0259291 A1 | 10/2009 | Kolbel et al. |
| 2009/0299449 A1 | 12/2009 | Styrc |
| 2010/0016943 A1 | 1/2010 | Chobotov |
| 2010/0023048 A1 | 1/2010 | Mach |
| 2010/0057195 A1 | 3/2010 | Roeder et al. |
| 2010/0082089 A1 | 4/2010 | Quadri et al. |
| 2010/0094394 A1 | 4/2010 | Beach et al. |
| 2010/0094401 A1 | 4/2010 | Kolbel et al. |
| 2010/0114290 A1 | 5/2010 | Rasmussen et al. |
| 2010/0145434 A1 | 6/2010 | Thornton et al. |
| 2010/0211052 A1 | 8/2010 | Brown et al. |
| 2010/0280591 A1 | 11/2010 | Shin et al. |
| 2011/0034987 A1 | 2/2011 | Kennedy |
| 2011/0040366 A1 | 2/2011 | Goetz et al. |
| 2011/0054515 A1 | 3/2011 | Bridgeman et al. |
| 2011/0054519 A1 | 3/2011 | Neuss |
| 2011/0066221 A1 | 3/2011 | White et al. |
| 2011/0094401 A1 | 4/2011 | Möhringer et al. |
| 2011/0125252 A1 | 5/2011 | Goddard et al. |
| 2011/0130821 A1 | 6/2011 | Styrc |
| 2011/0288624 A1 | 11/2011 | Roeder et al. |
| 2011/0313503 A1 | 12/2011 | Berra et al. |
| 2012/0022630 A1 | 1/2012 | Wuebbeling |
| 2012/0022638 A1 | 1/2012 | Leewood et al. |
| 2012/0046652 A1 | 2/2012 | Sokel |
| 2012/0130473 A1 | 5/2012 | Norris et al. |
| 2012/0130474 A1 | 5/2012 | Buckley |
| 2012/0130475 A1 | 5/2012 | Shaw |
| 2012/0143305 A1 | 6/2012 | Berra et al. |
| 2012/0172965 A1 | 7/2012 | Kratzberg et al. |
| 2012/0172968 A1 | 7/2012 | Chuter et al. |
| 2012/0239133 A1 | 9/2012 | Cartledge et al. |
| 2012/0283773 A1 | 11/2012 | Van et al. |
| 2012/0296360 A1* | 11/2012 | Norris ............... A61F 2/97 606/191 |
| 2012/0323270 A1 | 12/2012 | Lee |
| 2013/0023981 A1 | 1/2013 | Dierking et al. |
| 2013/0046371 A1 | 2/2013 | Greenberg et al. |
| 2013/0073029 A1 | 3/2013 | Shaw |
| 2013/0123896 A1 | 5/2013 | Bloss et al. |
| 2013/0138138 A1 | 5/2013 | Clark et al. |
| 2013/0158647 A1 | 6/2013 | Norris et al. |
| 2013/0178889 A1 | 7/2013 | Miles et al. |
| 2013/0245666 A1 | 9/2013 | Arsen et al. |
| 2013/0245742 A1 | 9/2013 | Norris |
| 2013/0296912 A1 | 11/2013 | Ottma |
| 2014/0012303 A1 | 1/2014 | Heipl |
| 2014/0046360 A1 | 2/2014 | Van et al. |
| 2014/0180385 A1 | 6/2014 | Majercak |
| 2014/0194968 A1* | 7/2014 | Zukowski ............... A61F 2/954 623/1.11 |
| 2014/0277412 A1 | 9/2014 | Bortlein et al. |
| 2014/0296908 A1 | 10/2014 | Ottma et al. |
| 2014/0296909 A1 | 10/2014 | Heipl et al. |
| 2014/0379019 A1 | 12/2014 | Larsen et al. |
| 2015/0005809 A1 | 1/2015 | Ayres et al. |
| 2015/0005810 A1 | 1/2015 | Center et al. |
| 2015/0051695 A1 | 2/2015 | Shaw |
| 2015/0305749 A1 | 10/2015 | Alferness |
| 2015/0313738 A1 | 11/2015 | Cully et al. |
| 2016/0256301 A1* | 9/2016 | Roeder ............... A61F 2/07 |
| 2016/0278782 A1 | 9/2016 | Anderson et al. |
| 2016/0296352 A1* | 10/2016 | Ryan ............... A61F 2/95 |
| 2016/0331382 A1 | 11/2016 | Center et al. |
| 2017/0056153 A1 | 3/2017 | Vinluan et al. |
| 2017/0172724 A1 | 6/2017 | Cartledge et al. |
| 2017/0181751 A1 | 6/2017 | Larsen et al. |
| 2017/0281382 A1 | 10/2017 | Lostetter et al. |

(56) References Cited

U.S. PATENT DOCUMENTS

| | | |
|---|---|---|
| 2017/0367859 A1 | 12/2017 | Bloss et al. |
| 2018/0036113 A1 | 2/2018 | Burkart et al. |
| 2018/0071123 A1 | 3/2018 | Arbefeuille et al. |
| 2018/0071126 A1 | 3/2018 | Beard et al. |
| 2019/0321207 A1* | 10/2019 | Arbefeuille .......... A61F 2/9662 |
| 2021/0169669 A1 | 6/2021 | Cato et al. |
| 2021/0244553 A1 | 8/2021 | Wiehn et al. |
| 2022/0151762 A1 | 5/2022 | Gore et al. |

FOREIGN PATENT DOCUMENTS

| | | |
|---|---|---|
| CN | 102413794 A | 4/2012 |
| CN | 103347467 A | 10/2013 |
| CN | 103945798 A | 7/2014 |
| CN | 106102596 A | 11/2016 |
| CN | 106344208 A | 1/2017 |
| EP | 0664107 A1 | 7/1995 |
| EP | 0679372 A2 | 11/1995 |
| EP | 1441668 B1 | 1/2008 |
| EP | 1915113 B1 | 3/2010 |
| EP | 1358903 B1 | 11/2011 |
| EP | 2481381 A1 | 8/2012 |
| EP | 1474074 B1 | 4/2014 |
| EP | 2749251 B1 | 7/2016 |
| EP | 3064173 A1 | 9/2016 |
| EP | 2956198 B1 | 11/2017 |
| EP | 3278771 A1 | 2/2018 |
| FR | 2896405 A1 | 7/2007 |
| GB | 1355373 A | 6/1974 |
| GB | 1506432 A | 4/1978 |
| GB | 2344054 A | 5/2000 |
| GB | 2448520 A | 10/2008 |
| JP | 08-126704 A | 5/1996 |
| JP | 09-309054 A | 12/1997 |
| JP | 2001-506902 A | 5/2001 |
| JP | 2002-503114 A | 1/2002 |
| JP | 2002-518086 A | 6/2002 |
| JP | 2003-502107 A | 1/2003 |
| JP | 2004-167239 A | 6/2004 |
| JP | 2004-188219 A | 7/2004 |
| JP | 2007-518465 A | 7/2007 |
| JP | 2011-511663 A | 4/2011 |
| JP | 2011-511693 A | 4/2011 |
| JP | 2011-516202 A | 5/2011 |
| JP | 2014-501563 A | 1/2014 |
| JP | 2014-501565 A | 1/2014 |
| JP | 2014-502180 A | 1/2014 |
| JP | 2014-533189 A | 12/2014 |
| WO | 96/18361 A1 | 6/1996 |
| WO | 97/48350 A1 | 12/1997 |
| WO | 98/27894 A1 | 7/1998 |
| WO | 99/65420 A1 | 12/1999 |
| WO | 00/13613 A1 | 3/2000 |
| WO | 01/21109 A1 | 3/2001 |
| WO | 02/28317 A2 | 4/2002 |
| WO | 03/34948 A1 | 5/2003 |
| WO | 2003/101518 A1 | 12/2003 |
| WO | 2005/070336 A1 | 8/2005 |
| WO | 2005/072652 A1 | 8/2005 |
| WO | 2006/007389 A1 | 1/2006 |
| WO | 2007/092354 A2 | 8/2007 |
| WO | 2008/047092 A1 | 4/2008 |
| WO | 2008/063464 A2 | 5/2008 |
| WO | 2009/102441 A1 | 8/2009 |
| WO | 2009/126227 A2 | 10/2009 |
| WO | 2009/148594 A1 | 12/2009 |
| WO | 2010/001012 A1 | 1/2010 |
| WO | 2010/024881 A1 | 3/2010 |
| WO | 2010/041038 A1 | 4/2010 |
| WO | 2010/044854 A1 | 4/2010 |
| WO | 2010/063795 A1 | 6/2010 |
| WO | 2010/081041 A1 | 7/2010 |
| WO | 2010/090699 A1 | 8/2010 |
| WO | 2010/105195 A2 | 9/2010 |
| WO | 2011/031981 A1 | 3/2011 |
| WO | 2011/062858 A1 | 5/2011 |
| WO | 2012/065080 A2 | 5/2012 |
| WO | 2012/068257 A2 | 5/2012 |
| WO | 2012/065080 A3 | 7/2012 |
| WO | WO-2012136984 A1 * | 10/2012 | ............... A61F 2/95 |
| WO | 2012/174254 A1 | 12/2012 |
| WO | 2013/040431 A1 | 3/2013 |
| WO | 2013/074266 A1 | 5/2013 |
| WO | 2013/137977 A1 | 9/2013 |
| WO | 2015/132668 A1 | 9/2015 |
| WO | 2018/005779 A1 | 1/2018 |
| WO | 2018/165358 A1 | 9/2018 |

OTHER PUBLICATIONS

International Preliminary Report on Patentability received for PCT Patent Application No. PCT/US2018/049057, mailed on Mar. 11, 2021, 9 pages.

International Search Report and Written Opinion received for PCT Patent Application No. PCT/US2018/049053, mailed on Apr. 25, 2019, 9 pages.

International Search Report and Written Opinion received for PCT Patent Application No. PCT/US2018/049057, mailed on Apr. 23, 2019, 14 pages.

Hsu et al., The Impact of Bird-Beak Configuration on Aortic Remodeling of Distal Arch Pathology After Thoracic Endovascular Aortic Repair with the Zenith Pro-FormTX2 Thoracic Endograft, Journal of Vascular Surgery, 2013, pp. 1-9.

International Search Report and Written Opinion for PCT/US2013/022404 mailed May 8, 2013, corresponding to U.S. Appl. No. 13/743,118, 7 pages.

International Search Report and Written Opinion for PCT/US2014/066153 mailed Feb. 17, 2015, corresponding to U.S. Appl. No. 14/084,592, 5 pages.

International Search Report and Written Opinion received for PCT Patent Application No. PCT/US2012/061928, mailed on Jan. 22, 2013, 8 pages.

International Search Report and Written Opinion received for PCT Patent Application No. PCT/US2018/021442, mailed on Jul. 11, 2018, 8 pages.

International Search Report PCT/US2013/022404 mailed May 8, 2013, corresponding to U.S. Appl. No. 13/743,118.

Thread. (n.d) American Heritage (r) Dictionary of the English Language, Fifth Edition. (2011). Retrieved Feb. 14, 2016 from http://www.thefreedictionary.com/thread.

Ueda, et al., Incomplete Endograft Apposition to the Aortic Arch: Bird-Beak Configuration Increases Risk of Endoleak Formation after Thoracic Endovascular Aortic Repair, Radiology: vol. 255: No. 2; May 2010, pp. 645-652.

European Search Report for EP Patent Application No. 24162997.1, Issued on Jun. 19, 2024, 12 pages.

* cited by examiner

STEERING WIRE ATTACH FOR ANGULATION

CROSS-REFERENCE TO RELATED APPLICATION

This application is a continuation of International Application PCT/US2018/021442 filed Mar. 8, 2018, which claims the benefit of U.S. Provisional Application No. 62/468,618, filed Mar. 8, 2017, both of which are herein incorporated by reference in their entirety.

TECHNICAL FIELD

The present invention relates to medical devices and methods for treating an anatomical space (e.g., vessels) of the body. More specifically, the invention relates to methods, apparatuses, and systems that include a prosthesis that allows for accurate deployment to treat dissections and aneurysms in the anatomical space.

BACKGROUND

Disease of the vasculature is increasingly common. Treatment of the vasculature may be difficult because of the tortuous nature and complexity of the vasculature. Aortic dissections, for example, commonly begin at or near the aortic valve root and continue to the ascending aorta and the aortic arch, and may also affect the upper part of the descending aorta. Medical devices implanted at a diseased state may be used for treatment of aortic dissections, aneurysms, and other diseases of the vasculature.

It remains desirable to provide medical devices, systems and methods for repairing disease along the aorta and also for repairing disease along the aorta and the branches extending therefrom.

SUMMARY

Various aspects of the present disclosure are directed toward delivery systems. A delivery system, as discussed in further detail below, may include a catheter having a leading end and a trailing end. The delivery system may also include an expandable device arranged near the leading end of the catheter and including a proximal end, a distal end, and a flow lumen extending therebetween. In addition, the delivery system may include an actuation wire coupled to the expandable device at one or more locations thereon with the actuation wire being configured to steer the expandable device during delivery thereof. Further, the delivery system may include at least one tether arranged through a portion of the expandable device arranged through the actuation wire and configured to couple the actuation wire to the expandable device.

Aspects of the disclosure are also directed toward a delivery system that includes a catheter having a leading end and a trailing end and an expandable device arranged near the leading end of the catheter. The expandable device may include a proximal end, a distal end, and a flow lumen extending therebetween. The delivery system may also include an actuation wire coupled to the expandable device at two or more locations thereon, the actuation wire being configured to steer the expandable device during delivery thereof.

Various aspects of the present disclosure are directed toward methods of deploying an expandable medical device at a tortious target location within a patient. The method may include delivering the expandable medical device to the tortious target location and manipulating an actuation wire, coupled to the expandable medical device, to arrange an end of the expandable medical device approximately perpendicular to an inflection point in the curvature of the tortious target location.

According to one example ("Example 1"), a delivery system includes: a catheter having a leading end and a trailing end; an expandable device arranged near the leading end of the catheter and including a proximal end, a distal end, and a flow lumen extending therebetween; an actuation wire coupled to the expandable device at one or more locations thereon, the actuation wire being configured to steer the expandable device during delivery thereof; and at least one tether arranged through a portion of the expandable device arranged through the actuation wire and configured to couple the actuation wire to the expandable device.

According to another example ("Example 2"), further to Example 1, the expandable device is configured to deploy at a tortious vessel having a curvature with at least one inflection point, and the actuation wire is configured to maintain the proximal end of the expandable device approximately perpendicular to the inflection point in the curvature of the tortious vessel during delivery of the expandable device.

According to another example ("Example 3"), further to any one of Examples 1-2, the actuation wire is coupled to the expandable device adjacent the proximal end via the at least one tether being arranged through the actuation wire and the portion of the expandable device.

According to another example ("Example 4"), further to any one of Examples 1-3, the actuation wire is configured to bidirectionally steer the expandable device proximally and distally during delivery thereof.

According to another example ("Example 5"), further to any one of Examples 1-4, the at least one tether includes two tethers, and the actuation wire coupled to the expandable device at two or more locations via the two tethers.

According to another example ("Example 6"), further to Example 5, the actuation wire includes a bifurcation including a first branch and a second branch, and the first branch and the second branch are coupled to the expandable device at the two or more locations via a first of the two tethers being arranged through the first branch, and a second of the two tethers being arranged through the second branch.

According to another example ("Example 7"), further to any one of Examples 1-6, the at least one tether is arranged through the actuation wire and arranged through the expandable device at the two locations to couple the actuation wire to the expandable device.

According to another example ("Example 8"), further to Example 7, the at least one tether extends from and through the actuation wire and through the expandable device at the two locations adjacent the proximal end of the expandable device.

According to another example ("Example 9"), further to Example 7, the at least one tether includes two tethers, and the two tethers extend from and through the actuation wire and through the expandable device at the two locations adjacent the proximal end of the expandable device.

According to another example ("Example 10"), further to any one of Examples 1-9, the at least one tether comprises a bio-absorbable material.

According to another example ("Example 11"), further to any one of Examples 1-10, the at least one tether is configured to uncouple and release from the expandable device in response to tension applied to the actuation wire after delivery of the expandable device.

According to another example ("Example 12"), further to any one of Examples 1-10, the actuation wire bifurcates to form a first branch and a second branch to form a y-shaped structure, and the first branch and the second branch are coupled to the expandable device at two locations.

According to another example ("Example 13"), further to Example 12, further including two tethers arranged configured to couple the actuation wire to the two or more locations on the expandable device.

According to another example ("Example 14"), further to Example 13, a first of the two tethers is arranged through a proximal end of the first branch and through the expandable device, and a second of the two tethers is arranged through a proximal end of the second branch and through the expandable device to couple the actuation wire to the two or more locations on the expandable device.

According to another example ("Example 15"), further to any one of Examples 1-14, the actuation wire includes an eyelet, and the at least one tether arranged through the eyelet of the actuation wire to couple the actuation wire to the expandable device.

According to another example ("Example 16"), a delivery system includes: a catheter having a leading end and a trailing end; an expandable device arranged near the leading end of the catheter and including a proximal end, a distal end, and a flow lumen extending therebetween; and an actuation wire coupled to the expandable device at two or more locations thereon, the actuation wire being configured to steer the expandable device during delivery thereof.

According to another example ("Example 17"), further to Example 16, wherein the actuation wire bifurcates to form a first branch and a second branch to form a y-shaped structure, and the first branch and the second branch are coupled to the expandable device at two locations.

According to another example ("Example 18"), further to Example 17, further including two tethers arranged configured to couple the actuation wire to the two or more locations on the expandable device.

According to another example ("Example 19"), further to Example 18, a first of the two tethers being arranged through a proximal end of the first branch and through the expandable device, and a second of the two tethers being arranged through a proximal end of the second branch and through the expandable device to couple the actuation wire to the two or more locations on the expandable device.

According to another example ("Example 20"), further to Example 17, further including at least one tether arranged through the actuation wire and arranged through the expandable device at two locations to couple the actuation wire to the expandable device.

According to another example ("Example 21"), further to Example 20, the at least one tether and the actuation wire form a y-shaped structure.

According to another example ("Example 22"), a method of deploying an expandable medical device at a tortuous target location within a patient where the method includes: delivering the expandable medical device to the tortuous target location; and manipulating an actuation wire, coupled to the expandable medical device, to arrange an end of the expandable medical device approximately perpendicular to an inflection point in the curvature of the tortious target location.

According to another example ("Example 23"), further to Example 22, where the step of manipulating the actuation wire includes bidirectionally steering the expandable medical device relative to the inflection point in the curvature of the tortious target location.

According to another example ("Example 24"), further to Example 22, where the step of manipulating the actuation wire includes actuating the expandable medical device by applying force to two or more locations on the expandable medical device.

According to another example ("Example 25"), further to Example 22, further including releasing the actuation wire from the expandable medical device by releasing a tether configured to couple the actuation wire to the expandable medical device.

DETAILED DESCRIPTION

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

Various aspects of the present disclosure are directed toward apparatuses, systems, and methods that include an expandable device that may be used in treatment of the vasculature. The expandable device is delivered to the vasculature using a delivery system. The delivery system may be configured to position and/or steer the expandable device for accurate placement in the vasculature. The expandable device may include a flow lumen between ends of the expandable device. The delivery system may be configured to arrange the expandable device such that one or both of the ends of the expandable device is perpendicular to a portion of the vasculature.

In addition, the expandable devices described herein may be substantially cylindrical or include a bifurcation. Further, the expandable devices may be configured to conform to the vasculature into which the expandable device is implanted, low-profile in order to enable delivery thereof using a minimally invasive procedure (e.g., transcatheter), and withstand forces and other stresses that occur once implanted in the vasculature.

Figure 1:
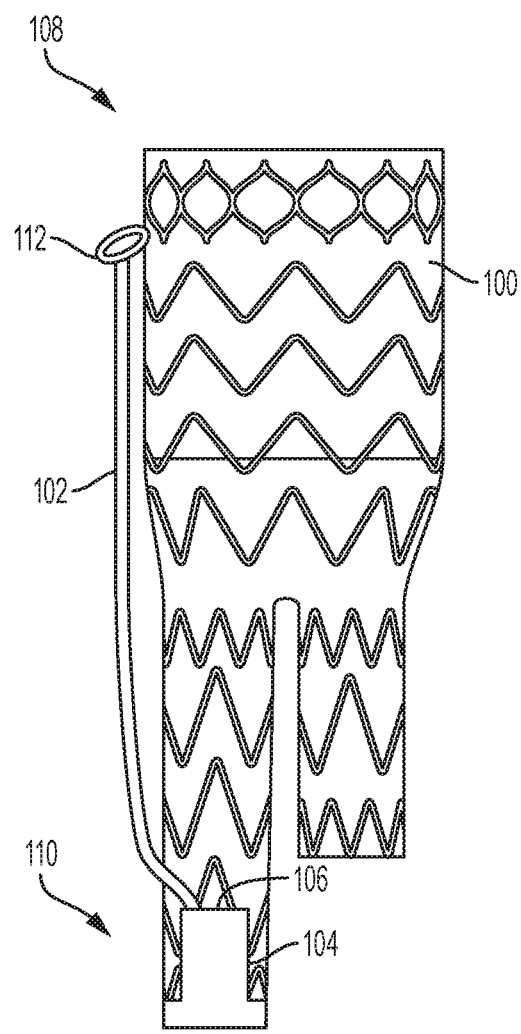
FIG. 1 shows an expandable device and an actuation wire in accordance with various aspects of the present disclosure.

FIG. 1 shows an expandable device 100 and an actuation wire 102 in accordance with various aspects of the present disclosure. The expandable device 100 is releasably coupled to a delivery system for delivery of the expandable device 100 to a target location within a patient's vasculature. The delivery system may include a catheter 104 that includes a leading end 106 and a trailing end (not shown in FIG. 1). The expandable device 100 may be arranged near the leading end 106 of the catheter 104. The catheter 104 may extend through a lumen of the expandable device 100 toward and past a proximal end 108 of the expandable device 100. The catheter 104 may also include a tip (not shown) at the leading end 106.

The expandable device 100 may include a proximal end 108, a distal end 110, and a flow lumen extending therebetween. The proximal end 108 of the expandable device 100 may be considered the end of the expandable device 100 that is closest to the target location within the patient's vasculature. The actuation wire 102 is coupled to the expandable device 100 at one or more locations thereon. As shown in FIG. 1, the actuation wire 102 is attached adjacent to or near the proximal end 108 of the expandable device 100 and accessible to a user of the delivery system.

As shown, the actuation wire 102 is coupled to the expandable device 100 via at least one tether 112. The tether 112 may be arranged through a portion of the expandable device 100 and through the actuation wire 102 to couple the actuation wire 102 to the expandable device 100. In certain instances and as shown in FIG. 1, the at least one tether 112 is arranged through the expandable device 100 near or adjacent to the proximal end 108 of the expandable device 100. The at least one tether 112 may be a single tether, as shown in FIG. 1.

In certain instances, the actuation wire 102 is configured to steer the expandable device 100 during delivery thereof. The actuation wire 102 may include a stiffness such that a user operating the delivery system may apply force to the actuation wire 102 and bidirectionally steer (e.g., proximally and distally relative to the target location within the patient's vasculature) the expandable device 100. For example, the actuation wire 102 may have a stiffness that is greater than a stiffness of the tether 112. The stiffness of the actuation wire 102 and/or the location to which the actuation wire 102 is coupled to the expandable device 100 may facilitate deploying and arranging the expandable device 100 relative to the target location within the patient's vasculature. For example, the expandable device 100 may be configured to deploy at a tortious vessel having a curvature with at least one inflection point. In certain instances, the actuation wire 102 is configured to maintain the proximal end 108 of the expandable device 100 approximately perpendicular to the inflection point in the curvature of the tortious vessel during delivery of the expandable device 100.

The actuation wire 102 may be uncoupled or released from the actuation wire 102 subsequent to the expandable device 100 being positioned and deployed at the target location within the patient's vasculature and removed from the patient. In certain instances, the tether 112 is configured to remain coupled or threaded through the expandable device 100 after the actuation wire 102 is released or uncoupled from the expandable device 100 (e.g., as shown in further detail in FIG. 8). In addition, the tether 112 may be formed from a bio-absorbable material that dissolves to release or uncouple the actuation wire 102 from the expandable device 100. In other instances, the tether 112 is configured to be removed or unthreaded from the expandable device 100 after the actuation wire 102 is released or uncoupled from the expandable device 100 (e.g., as shown in further detail in FIGS. 9A-D and FIGS. 10A-C).

Figure 2:
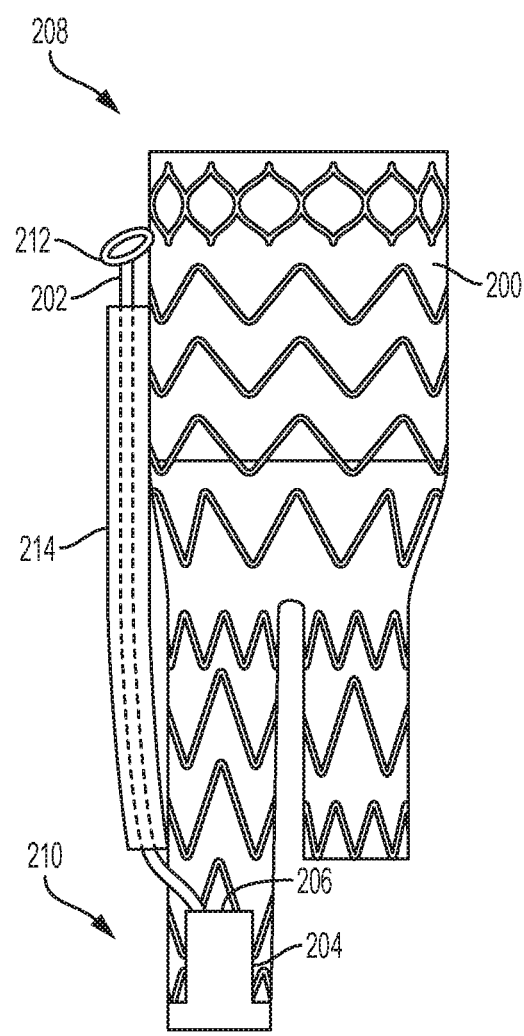
FIG. 2 shows another expandable device and an actuation wire in accordance with various aspects of the present disclosure.

FIG. 2 shows another expandable device 200 and an actuation wire 202 in accordance with various aspects of the present disclosure. The expandable device 200 may be releasably coupled to a delivery system. The delivery system may include a catheter 204 that includes a leading end 206 and a trailing end (not shown in FIG. 2). The expandable device 200 may be arranged near the leading end 206 of the catheter 204. The delivery system may be configured to deliver the expandable device 200 to a target location within a patient's vasculature. In certain instances, the expandable device 200 may be configured to deploy at a tortious vessel having a curvature with at least one inflection point. To facilitate deploying of the expandable device 200, the delivery system may include the actuation wire 202 configured to maintain a proximal end 208 (or distal end 210) of the expandable device 200 approximately perpendicular to the inflection point in the curvature of the tortious vessel during delivery of the expandable device 200.

The actuation wire 202 (and accessible to a user of the delivery system), for example, is configured to steer the expandable device 200 during delivery thereof, and is releasably coupled to the expandable device 200 via at least one tether 212. The tether 212 may be arranged through a portion of the expandable device 200 and through the actuation wire 202 to couple the actuation wire 202 to the expandable device 200. In certain instances and as shown in FIG. 2, the at least one tether 212 is arranged through the expandable device 200 near or adjacent to the proximal end 208 of the expandable device 200. In certain instances, the tether 212 is configured to remain coupled or threaded through the expandable device 200 after the actuation wire 102 is released or uncoupled from the expandable device 200 (e.g., as shown in further detail in FIG. 8) or the tether 212 may be configured to be removed or unthreaded from the expandable device 200 after the actuation wire 202 is released or uncoupled from the expandable device 200 (e.g., as shown in further detail in FIGS. 9A-D and FIGS. 10A-C).

In addition, the actuation wire 202 may be arranged through a sleeve 214 that is attached to an exterior portion of the expandable device 200. The expandable device 200 may include a graft component and one or more stent components (e.g., as shown in further detail with reference to FIG. 5). The sleeve 214 may be formed of a similar material or the same material as the graft component of the expandable device 200. The sleeve 214 may include a lumen through which the actuation wire 202 is arranged. In certain instances, the sleeve 214 is an enclosed structure which forms the lumen, or the sleeve 214 is a layer of graft material that forms a lumen between the sleeve 214 and the expandable device 200. The sleeve 214 may facilitate the actuation wire 202 steering the expandable device 200. The sleeve 214 may prevent traumatic interaction between the actuation wire 202 and a vessel wall. In addition, the sleeve 214 may enhance the connection between the actuation wire 202 and the expandable device 200 when a user applies force or tension to the actuation wire 202. As shown, the sleeve 214 has a length similar to a length of the expandable device 200. In other instances, the sleeve 214 may have a shorter length than the expandable device 200 or a longer length than the expandable device.

The actuation wire 202 may include a stiffness such that a user operating the delivery system may apply force to the actuation wire 202 and bidirectionally steer (e.g., proximally and distally relative to the target location within the patient's vasculature) the expandable device 200. For example, the actuation wire 202 may have a stiffness that is greater than a stiffness of the tether 212. The stiffness of the actuation wire 202 and/or the location to which the actuation wire 202 is coupled to the expandable device 200 may facilitate deploying and arranging the expandable device 200 relative to the target location within the patient's vasculature.

Figure 3:
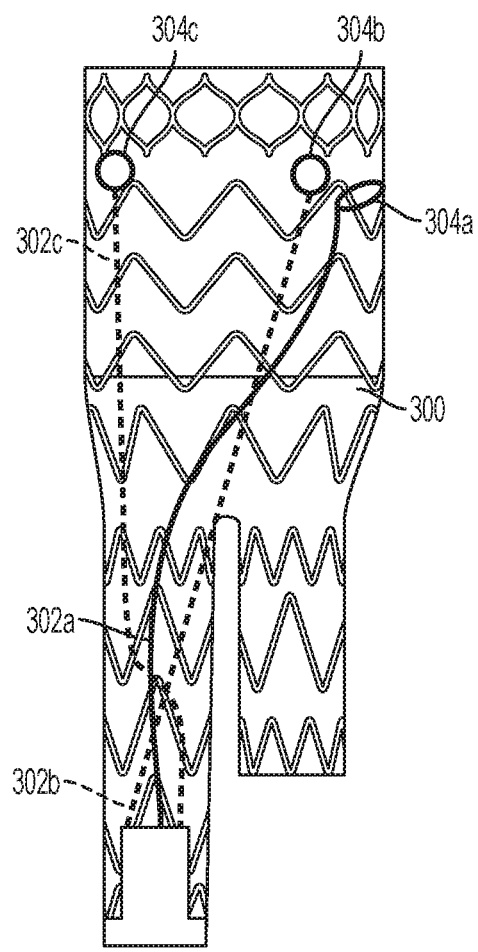
FIG. 3 shows yet another expandable device and an actuation wire in accordance with various aspects of the present disclosure.

FIG. 3 shows yet another expandable device 300 and an actuation wire 302a-c in accordance with various aspects of the present disclosure. The actuation wire 302a-c is shown arranged along the expandable device 300 in three different patterns. The patterns of the actuation wire 302a-c shown in FIG. 3 may facilitate the ability of the actuation wire 302a-c to steer the expandable device by distributing forces that result from a user applying force or tension to the actuation wire 302a-c to steer the expandable device 300 (e.g., as described above in detail with reference to FIGS. 1-2).

The actuation wire 302a-c may be attached to the expandable device 300 via a tether 304a-c. The tether 304a-c may be arranged through the actuation wire 302a-c at any portion along a length thereof that is in contact with the expandable device 300.

The illustrative expandable device 300 and actuation wire 302a-c shown in FIG. 3 is not intended to suggest any limitation as to the scope of use or functionality of embodiments of the discussed throughout this disclosure. Neither should the illustrative expandable device 300 and actuation wire 302 be interpreted as having any dependency or requirement related to any single component or combination of components illustrated therein. For example, in various embodiments, the illustrative actuation wire 302a-c may include a stiffness and bidirectional steering as described above with reference to FIGS. 1-2. Additionally, any one or more of the components depicted in FIG. 3 can be integrated with various ones of the other components depicted therein (and/or components not illustrated). For example, the patterns of the actuation wire 302a-c may be used in connection with the actuation wires 102, 202 shown in FIGS. 1-2.

FIGS. 4A-E shows side view illustrations of expandable device angulation relative to a target location 400a-e in accordance with various aspects of the present disclosure. Each of FIGS. 4A-E show a side profile of a leading (or proximal) end 400a-e of an expandable device, consistent with various aspects of the present disclosure. In certain instances, the target location 400a-e may be at a tortious vessel of a patient. The target location 400a-e into which the expandable device is implanted may have angulation (e.g., a curvature with at least one inflection point 404a-e). The target location 400a-e may be an angulated abdominal aortic aneurism (AAA).

Figure 4A:
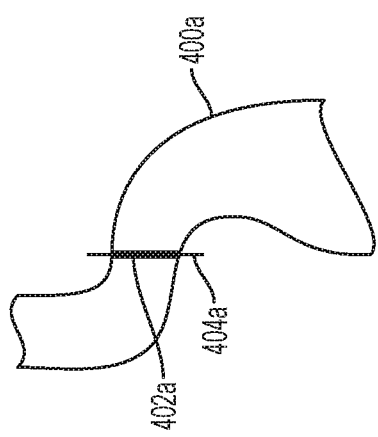
FIGS. 4A-E shows side view illustrations of expandable device angulation relative to a target location in accordance with various aspects of the present disclosure.
Figure 4E:
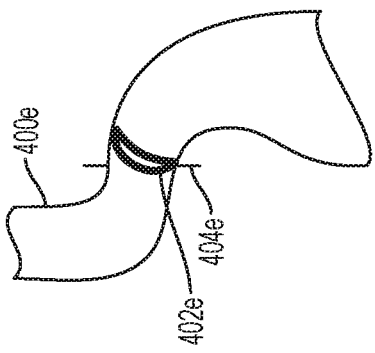
Figure 4D:
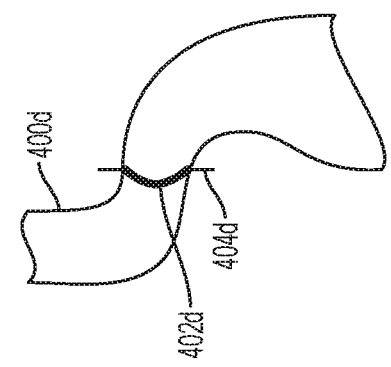
Figure 4C:
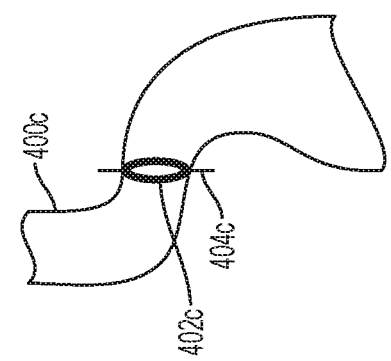
Figure 4B:
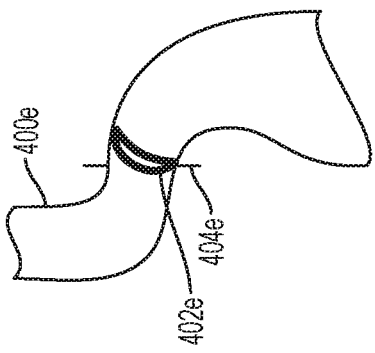

In certain instances, one of the ends 402a-e of the expandable device may be deployed perpendicular to the inflection point in the curvature of the tortious vessel during delivery of the expandable device. Non-perpendicularity may negatively affect the ability of the expandable device to seal against the target location 400a-e. FIG. 4A shows the leading (or proximal) end 402a deployed perpendicular to the inflection point 404a. In certain instances, perpendicularity of the expandable device may be a function of device flatness, angulation, and rotational alignment. FIG. 4B shows the leading (or proximal) end 402b of an expandable device angled relative to the inflection point 404b of the target location 400b. FIG. 4C shows the leading (or proximal) end 402c of an expandable device rotated relative to the inflection point 404c of the target location 400c. FIG. 4D shows the leading (or proximal) end 402d of an expandable device deformed relative to the inflection point 404b of the target location 400d. FIG. 4E shows the leading (or proximal) end 402e of an expandable device deformed or flat, rotated, and angled relative to the inflection point 404e of the target location 400e.

Device deployment and performance can be enhanced by steering the device to an appropriate location while maintaining one of the ends of the expandable device perpendicular to the target location 400a-e (e.g., curvature of a vessel with at least one inflection point 404a-e) during and after deployment. The actuation wires and arrangements thereof discussed herein facilitate maintaining the expandable device perpendicular during and after deployment (as shown in FIG. 4A) and mitigate against non-perpendicular, angled, or flat deployment (as shown in FIGS. 4B-E).

Figures 5A, 5B:
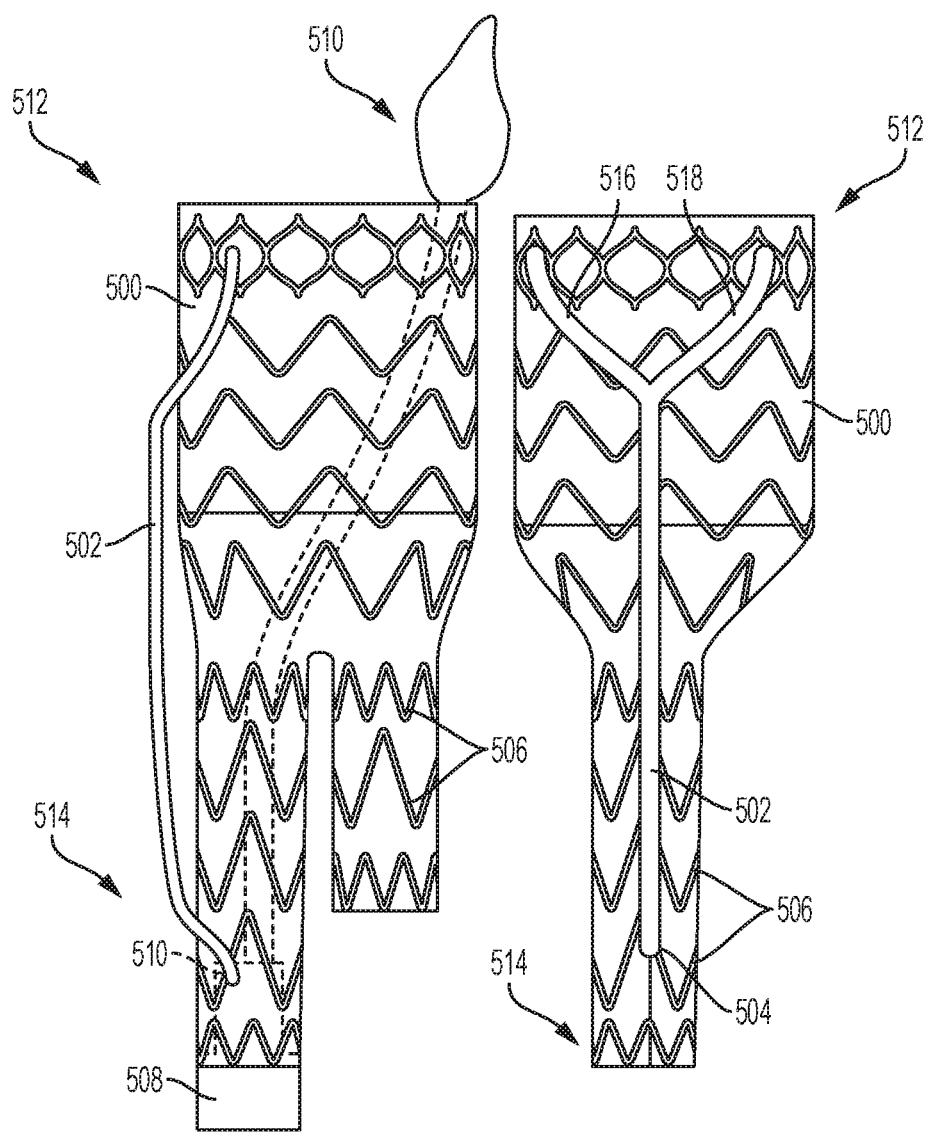
FIG. 5A shows a front view of an expandable device and an actuation wire in accordance with various aspects of the present disclosure.
FIG. 5B shows a side view of the expandable device and the actuation wire, shown in FIG. 5A, in accordance with various aspects of the present disclosure.

FIGS. 5A-B show a side view and a front view of an expandable device 500 and an actuation wire 502 in accordance with various aspects of the present disclosure. The expandable device 500 may include a graft component 504 and one or more stent components 506. The delivery system may include a catheter 508 that includes a leading end 510 and a trailing end (not shown in FIGS. 5A-B). The expandable device 500 may be arranged near the leading end 510 of the catheter 508. In addition, the expandable device 500 may include a proximal end 512, a distal end 514, and a flow lumen extending therebetween. The proximal end 512 of the expandable device 500 is considered the end of the expandable device 500 closest to the target location within the patient's vasculature. The actuation wire 502 is configured to releasably couple the expandable device 500 to the delivery system for delivery of the expandable device 500 to a target location within a patient's vasculature and accessible to a user of the delivery system.

In certain instances, the actuation wire 502 is coupled to the expandable device 500 at one or more locations thereon. As shown in FIG. 5B, the actuation wire 502 bifurcates to form a first branch 516 and a second branch 518. The first branch 516 and the second branch 518 are coupled to the expandable device 500 at the two or more locations thereon. The first branch 516 and the second branch 518 are coupled to the expandable device 500 near the proximal end 512. In addition, the actuation wire 502 is configured to steer the expandable device 500 during delivery thereof. The first branch 516 and the second branch 518 may facilitate the ability of the actuation wire 502 to steer the expandable device 500 by distributing forces that result from a user manipulating or applying force to the actuation wire 502 to steer the expandable device 500.

In certain instances, one of the proximal end 512 and the distal end 514 of the expandable device 500 may be deployed perpendicular to a portion of the target location. The target location may be tortious vessel, which may include one or more inflection points in the curvature of the tortious vessel. In certain instances, perpendicularity of an end of the expandable device 500 is enhanced by the actuation wire 502 being configured to steer the expandable device 500 to the target location while maintaining one of the ends (the proximal end 512 or the distal end 514) of the expandable device 500 perpendicular to the target location. The first branch 516 and the second branch 518 may facilitate maintaining the expandable device perpendicular during and after deployment (as shown in FIG. 4A) and mitigate against non-perpendicular deployment (as shown in FIGS. 4B-E).

The first branch 516 and the second branch 518 may distribute forces applied to the actuation wire 502 in steering the expandable device 500. For example, a user operating the delivery system may apply force to the actuation wire 500 and bidirectionally steer (e.g., proximally and distally relative to the target location within the patient's vasculature) the expandable device 500. The actuation wire 502 is configured to remain in tension through a length thereof when force is applied to the actuation wire 502 by the user. The actuation wire 502, for example, may have a stiffness such that the actuation wire 502 does not become relaxed or slacked in response to the user applying force (e.g., tension) to steer the expandable device 500 proximally and distally.

In certain instances, the actuation wire 502 is coupled to the expandable device 500 via an adhesive (e.g., fluorinated ethylene propylene (FEP)). Each of the first branch 516 and the second branch 518 are releasably adhered to the expandable device 500 along any portion thereof. In certain instances, portions of the actuation wire 502 are arranged through expandable device 500. The portions may be the first branch 516 and the second branch 518 threaded through the graft component 504. After the user has steered the expandable device 500 to a desired location and after deployment thereof, the actuation wire 502 may be released from the expandable device 500 and removed from the patient. In certain instances where the actuation wire 502 is directly attached to the expandable device 500, and when force applied by the user, in excess of the force used to steer, may release the actuation wire 502. Friction between the target location (e.g., vessel wall) and the expandable device 500 may allow user to apply a greater force or tension to the actuation wire 502 than during steering to release the actuation wire 502.

Figure 8:
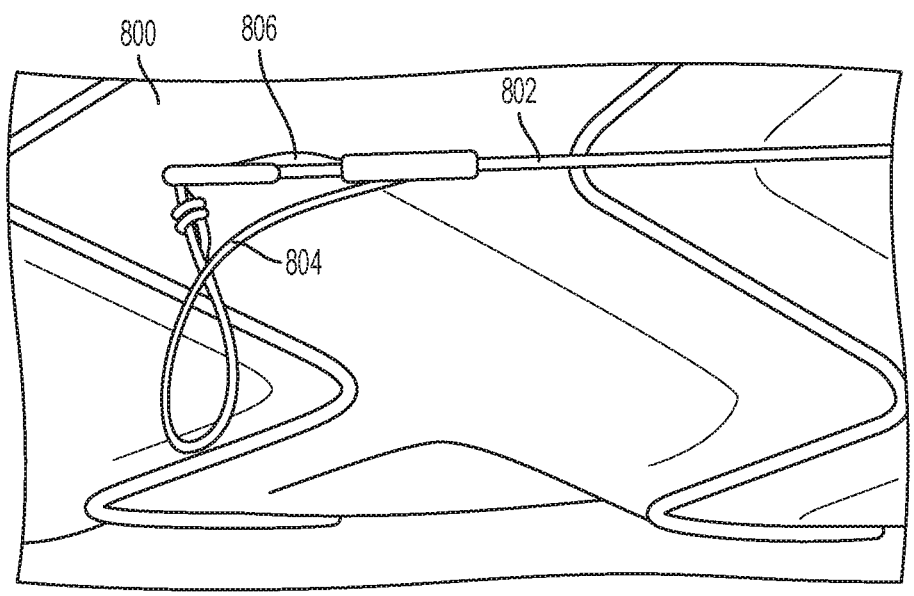
FIG. 8 shows an actuation wire and tether attachment to an expandable device in accordance with various aspects of the present disclosure.

In addition, the delivery system may include one or more tethers (not shown) arranged through a portion of the expandable device 500 and arranged through the actuation wire 502. The tethers (e.g., as shown in FIGS. 8-9) are configured to couple the actuation wire 502 to the expandable device 500. One of the tethers is arranged through the first branch 516, and a second of the two tethers is arranged through the second branch 518. The tethers may be arranged through the first branch 516 and the second branch 518 of the actuation wire 502 adjacent the proximal end 512 of the expandable device 500. In addition, the tethers may be configured to uncouple and release from the expandable device 500 in response to force or tension applied to the tethers after delivery of the expandable device. The tethers may break in response to the force or tension (and remain with the expandable device 500 after release of the actuation wire 502) or the tethers may unthread and be removed with the actuation wire 502 (e.g., as show in FIGS. 9A-D and FIGS. 10A-C).

Figures 6A, 6B:
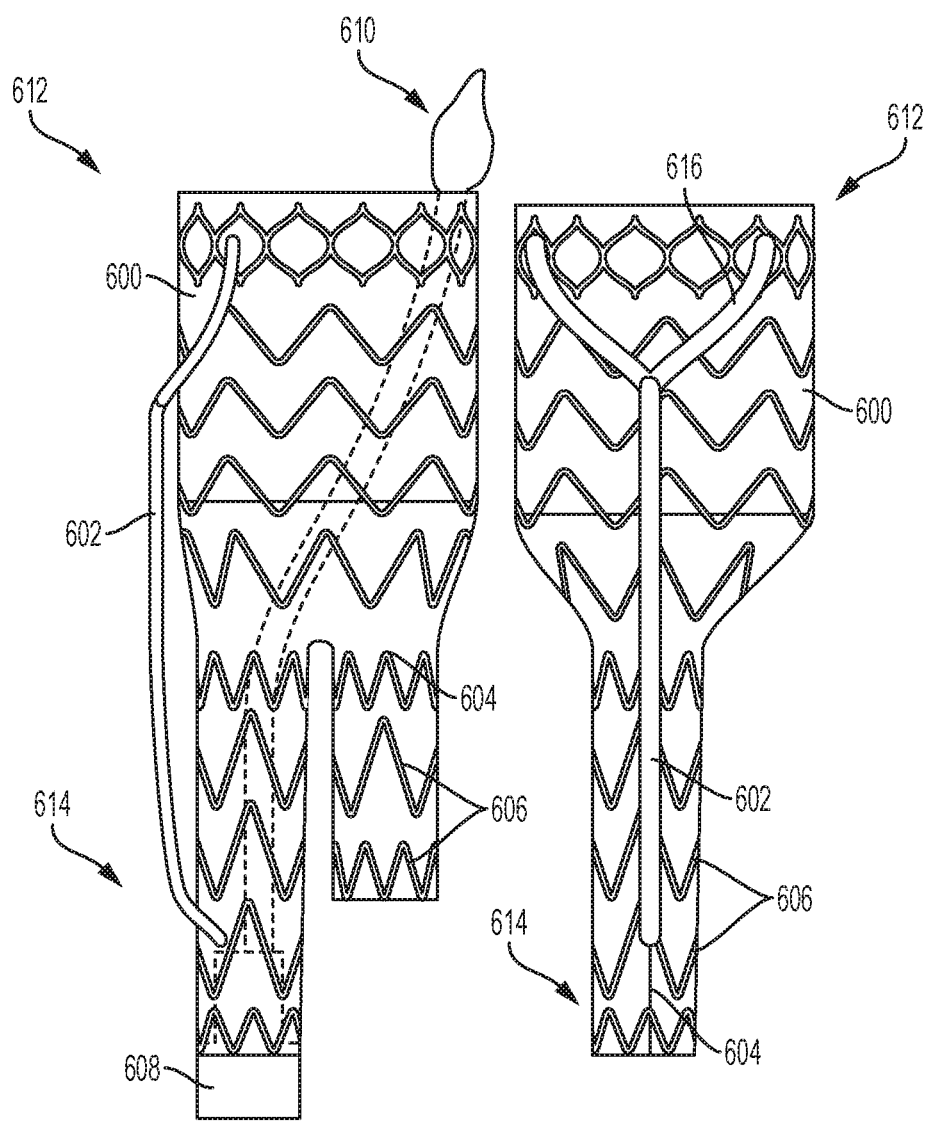
FIG. 6A shows a front view of another expandable device and an actuation wire in accordance with various aspects of the present disclosure.
FIG. 6B shows a side view of the expandable device and the actuation wire, shown in FIG. 6A, in accordance with various aspects of the present disclosure.

FIGS. 6A-B show a side view and a front view of an expandable device 600 and an actuation wire 602 in accordance with various aspects of the present disclosure. The expandable device 600 may include a graft component 604 and one or more stent components 606. The delivery system may include a catheter 608 with a portion 610 of the catheter 608 arranged through the expandable device 600. The actuation wire 602 may be configured to releasably couple the expandable device 600 to the delivery system for delivery of the expandable device 600 to a target location within a patient's vasculature. In addition, the expandable device 600 may include a proximal end 612, a distal end 614, and a flow lumen extending therebetween.

In certain instances, the actuation wire 602 is coupled to the expandable device 600 at one or more locations thereon and accessible to a user of the delivery system. The actuation wire 602 may be coupled to the expandable device 600 by at least one tether 616. As shown in FIG. 6B, the at least one tether 616 and the actuation wire 602 may form a y-shaped structure. In certain instances, the least one tether 616 is configured to couple the actuation wire 602 to the two or more locations on the expandable device 602. The least one tether 616 is secured to the actuation wire 602 or arranged through the actuation wire 602 (e.g., as shown in FIG. 8). In certain instances, the at least one tether 616 is a plurality of tethers (e.g., two tethers) coupled to the actuation wire 602. The least one tether 616 (or plurality of tethers) is coupled to the expandable device 600 adjacent the proximal end 612 thereof.

In addition, the actuation wire 602 is configured to steer the expandable device 600 during delivery thereof. The at least one tether 616 being coupled to two locations on the expandable device 600 may facilitate the ability of the actuation wire 602 to steer the expandable device 600 by distributing forces that result from a user applying force or tension to the actuation wire 602 to steer the expandable device 600. In certain instances, one of the proximal end 612 and the distal end 614 of the expandable device 600 are deployed perpendicular to a portion of the target location (e.g., a tortious vessel). Perpendicularity of the expandable device 600 may be enhanced by the actuation wire 602 being configured to steer the expandable device 600 to the target location while maintaining one of the ends (the proximal end 612 or the distal end 614) of the expandable device 600 perpendicular to the target location. Further, a user operating the delivery system may apply force to the actuation wire 600 and bidirectionally steer (e.g., proximally and distally relative to the target location within the patient's vasculature) the expandable device 600. The actuation wire 602 may be configured to remain in tension through a length thereof when tension is applied to the actuation wire 602 by the user.

After the user has steered the expandable device 600 to a desired location and after deployment thereof, the actuation wire 602 may be released from the expandable device 600 and removed from the patient. In certain instances, the force or tension applied to at least one tether 616 causes the tether 616 to uncouple from the expandable device 600.

Figure 7A:
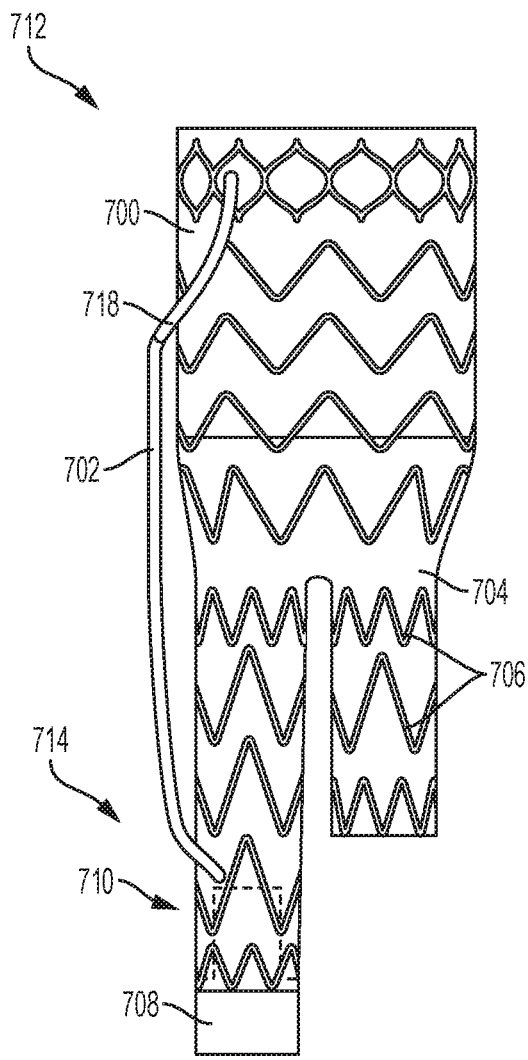
FIG. 7A shows a front view of yet another expandable device and an actuation wire in accordance with various aspects of the present disclosure.
Figure 7B:
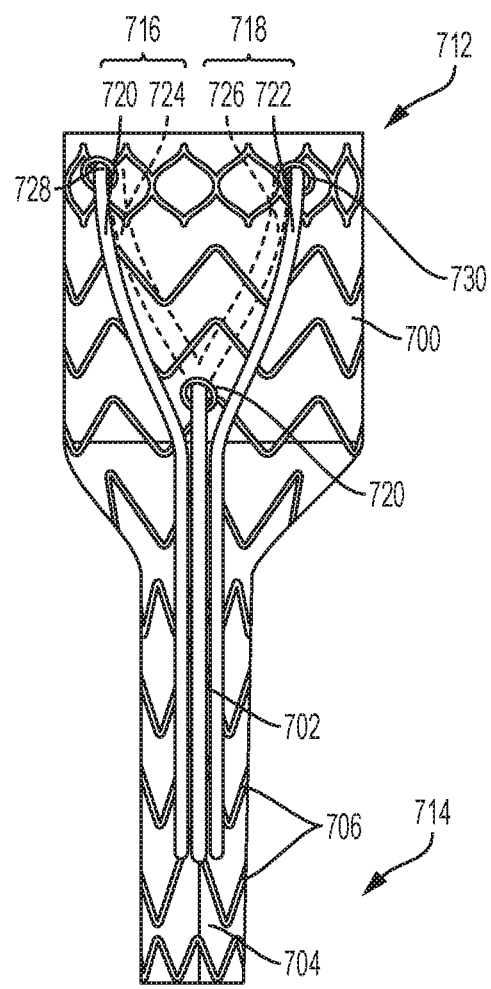
FIG. 7B shows a side view of the expandable device and the actuation wire, shown in FIG. 7A, in accordance with various aspects of the present disclosure.

FIGS. 7A-B show a side view and a front view of an expandable device 700 and an actuation wire 702 in accordance with various aspects of the present disclosure. The expandable device 700 may include a graft component 704 and one or more stent components 706. The delivery system may include a catheter 708 with a leading end 710 of the catheter 708 arranged near an end of the expandable device 700. The actuation wire 702 may be configured to releasably couple the expandable device 700 to the delivery system for delivery of the expandable device 700 to a target location within a patient's vasculature. In addition, the expandable device 700 may include a proximal end 712, a distal end 714, and a flow lumen extending therebetween.

The actuation wire 702 is configured to steer the expandable device 700 and is accessible to a user of the delivery system. In certain instances, one of the proximal end 712 and the distal end 714 of the expandable device 700 are deployed perpendicular to a portion of the target location (e.g., a tortious vessel). Further, a user operating the delivery system can apply force to the actuation wire 702 and bidirectionally steer (e.g., proximally and distally relative to the target location within the patient's vasculature) the expandable device 700. The actuation wire 702 may be configured to remain in tension through a length thereof when tension is applied to the actuation wire 702 by the user.

In addition, at least one tether 716 may be coupled to two (or more) locations 728, 730 on the expandable device 700 to facilitate the ability of the actuation wire 702 to steer the expandable device 700 by distributing forces that result from a user applying force to the actuation wire 702 to steer the expandable device 700.

In certain instances, tethers 716, 718 are configured to couple the actuation wire 702 to the expandable device 700. The tethers 716, 718 are arranged through the expandable device 700 (e.g., through the graft component 704) at one or locations thereon. The tethers 716, 718 may be arranged through the expandable device 700 near the proximal end 712. In addition, the tethers 716, 718 may extend from the proximal end 712 of the expandable device 700 and may also be accessible to the user. In addition and as shown in FIG. 6B, the at least one tethers 716, 718 and the actuation wire 702 may form a y-shaped structure.

The tethers 716, 718 may each include two portions. In certain instances, first portions 720, 722 of the tethers 716, 718 are arranged internal to the expandable device and may be accessible to the user, and second portions 724, 726 of the tethers 716, 718 are arranged between the eyelet 720 and an eyelet 720 of the actuation wire 702. In certain instances, the first portions 720, 722 and the second portions 724, 726 of the tethers 716, 718 are distinct threads attached or knotted together at the locations 728, 730 on the expandable device 700. The first portions 720, 722 and/or the second portions 724, 726 may be thread through the graft component 704. In other instances, the first portions 720, 722 and the second portions 724, 726 of the tethers 716, 718 are integral with one another and are thread through the graft component 704 at the locations 728, 730 on the expandable device 700.

After the user has steered the expandable device 700 to a desired location and after deployment thereof, the actuation wire 702 may be released from the expandable device 700 and removed from the patient. The user may apply tension to ends of the tethers 716, 718 to unthread the tethers 716, 718 from the expandable device 700 and through the eyelet 720. In various examples, the first portions 720, 722 and the second portions 724, 726 of the tethers 716, 718 are integral with one another and are concurrently releasable by tensioning the ends of the tethers 716, 718. In the instances where the first portions 720, 722 and the second portions 724, 726 of the tethers 716, 718 are attached or knotted together, tension is applied to the first portions 720, 722 of the tethers 716, 718 for release thereof. As a result, the first portions 720, 722 may release from the second portions 724, 726, and the first portions 720, 722 of the tethers 716, 718 may be removed from the expandable device 700.

The expandable device 700 shown in FIGS. 7A-B is not intended to suggest any limitation as to the scope of use or functionality of embodiments of the disclosure disclosed throughout this document. Neither should the illustrative prosthesis 200 be interpreted as having any dependency or requirement related to any single component or combination of components illustrated therein. For example, in some embodiments, the illustrative expandable device 700 may include additional components such as described in further detail with reference to FIGS. 1-6 and 8-9. Additionally, any one or more of the components depicted in FIGS. 7A-B can be, in embodiments, integrated with various ones of the other components depicted therein (and/or components not illustrated).

FIG. 8 shows an actuation wire 802 and tether 804 attachment to an expandable device 800 in accordance with various aspects of the present disclosure. The actuation wire 802 may include an eyelet 806 arranged at an end thereof. The tether 804 may be threaded through the eyelet 806 to releasably couple the expandable device 800 to a delivery system.

The tether 804 may also be threaded through the expandable device 800 to releasably couple the expandable device 800 to the delivery system. In other instances, the tether 804 is directly attached to the expandable device 800 via an adhesive. In addition, the actuation wire 802 may have a stiffness greater than a stiffness of the tether 804 as is described in further detail above.

Figure 9A:
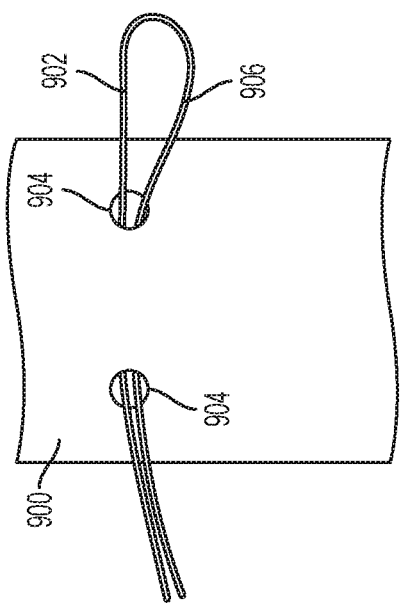
FIG. 9A-D show a tether attachment arrangement in accordance with various aspects of the present disclosure.
Figure 9B:
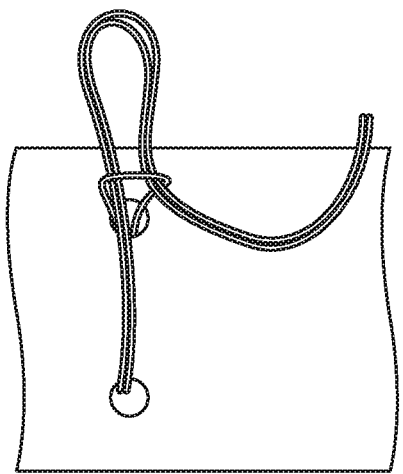
Figure 9C:
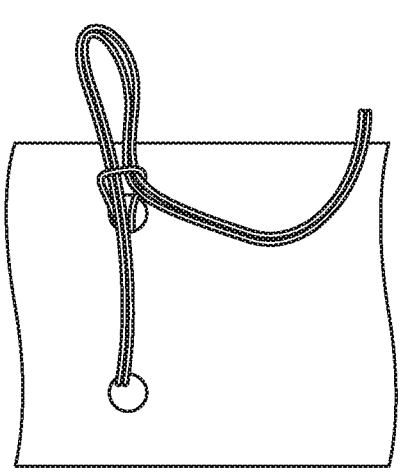
Figure 9D:
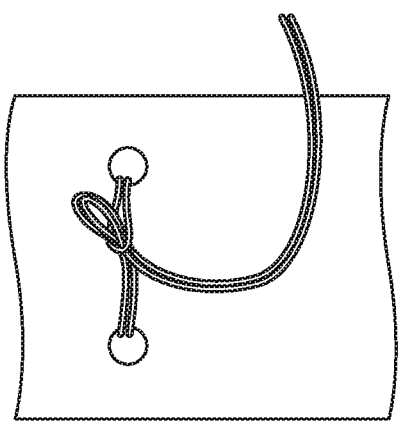

FIG. 9A-D show a tether attachment 902 arrangement in accordance with various aspects of the present disclosure. The tether attachment 902 may be threaded through an expandable medical device 900 at two locations 904. The tether attachment 902 may include a looped end 906. As shown in FIG. 9B, the tether attachment 902 is threaded through the looped end 906. As shown in FIG. 9C, the tether attachment 902 is threaded back through the looped end 906. As shown in FIG. 9D, the tether attachment 902 is pulled tight to form a releasable slip knot. The tether attachment 902 may be used to couple an expandable device to an actuation wire as discussed herein.

Figure 10A:
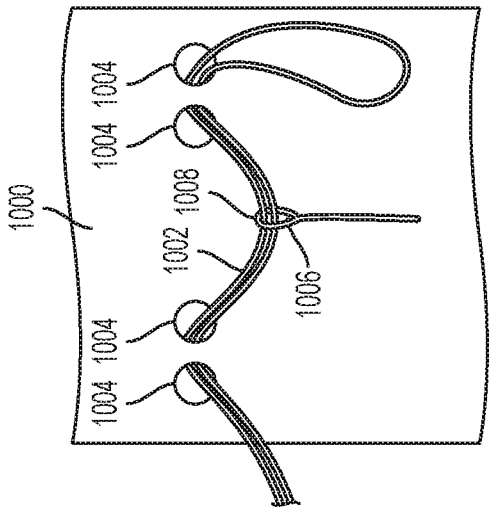
FIG. 10A-C show another tether attachment arrangement in accordance with various aspects of the present disclosure.
Figure 10B:
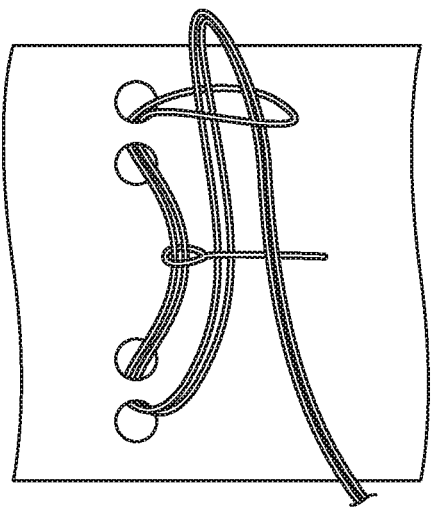
Figure 10C:
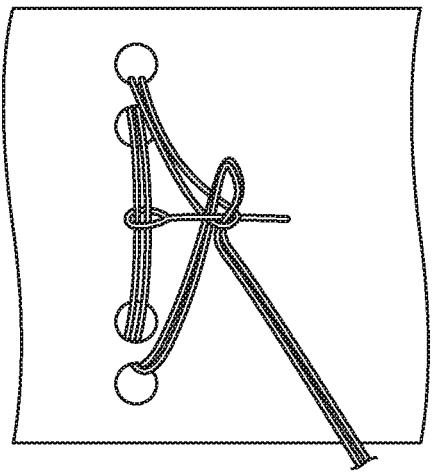

FIG. 10A-C show a tether attachment 1002 arrangement in accordance with various aspects of the present disclosure. The tether attachment 1002 may be threaded through an expandable medical device 1000 at four locations 1004. The tether attachment 1002 is threaded through the four locations 1004. The tether attachment 1002 may include a looped end 1010. The tether attachment 1002 may be used to couple an expandable device to an actuation wire 1006 as discussed herein. As shown in FIG. 10A, the tether attachment 1002 is arranged through an eyelet 1008 of the actuation wire 1006.

As shown in FIGS. 10B-C, the tether attachment 1002 is threaded through the looped end 1010, and then back therethrough. The tether attachment 1010 is pulled tight to form a releasable slip not. Other release mechanisms may be used to couple an actuation wire to an expandable medical device as discussed herein.

The actuation wires discussed herein may be formed from metallic, polymeric or natural materials such as stainless steels, cobalt-chromium alloys and nitinol. Further, actuation wires can also be formed from high strength polymer fibers such as ultra high molecular weight polyethylene fibers (e.g., Spectra™, Dyneema Purity™, etc.) or aramid fibers (e.g., Technora™, etc.).

The graft components may be made up of any material which is suitable for use as a graft in the chosen body lumen and being resistant to expansion as discussed herein. The graft components may be composed of the same or different materials. Furthermore, the graft components may include multiple layers of material that can be the same material or different material. In one embodiment, said materials can be used in combination and assembled together to comprise a graft. The graft materials used in a stent graft can be extruded, coated or formed from wrapped films, or a combination thereof. Polymers, biodegradable and natural materials can be used for specific applications.

Examples of synthetic polymers include, but are not limited to, nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a graft material. In one embodiment, said graft is made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. In another embodiment, said graft comprises expanded fluorocarbon polymers (especially PTFE) materials described in British. Pat. No. 1,355,373; 1,506,432; or 1,506,432 or in U.S. Pat. Nos. 3,953,566; 4,187,390; or 5,276,276, the entirety of which are incorporated by reference. Included in the class of preferred fluoropolymers are polytetrafluoroethylene (PTFE), fluorinated ethylene propylene (FEP), copolymers of tetrafluoroethylene (TFE) and perfluoro(propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is ePTFE. In another embodiment, said graft comprises a combination of said materials listed above. In another embodiment, said graft is substantially impermeable to bodily fluids. Said substantially impermeable graft can be made from materials that are substantially impermeable to bodily fluids or can be constructed from permeable materials treated or manufactured to be substantially impermeable to bodily fluids (e.g. by layering different types of materials described above or known in the art). In another embodiment, said outermost tube comprises ePTFE. In another embodiment, said innermost tube comprises ePTFE. In another embodiment, said innermost and outermost tube comprises ePTFE film that has been wrapped into a tube. In another embodiment, said secondary stent is covered with any of the material disclosed herein or known in the art. In another embodiment, the secondary stent covering comprises ePTFE.

Additional examples of graft materials include, but are not limited to, vinylidinefluoride/hexafluoropropylene hexafluoropropylene (HFP), tetrafluoroethylene (TFE), vinylidenefluoride, 1-hydropentafluoropropylene, perfluoro (m ethyl vinyl ether), chlorotrifluoroethylene (CTFE), pentafluoropropene, trifluoroethylene, hexafluoroacetone, hexafluoroisobutylene, fluorinated poly(ethylene-co-propylene (FPEP), poly(hexafluoropropene) (PHFP), poly(chlorotrifluoroethylene) (PCTFE), poly(vinylidene fluoride (PVDF), poly(vinylidene fluoride-co-tetrafluoroethylene) (PVDF-TFE), poly(vinylidene fluoride-co-hexafluoropropene) (PVDF-HFP), poly(tetrafluoroethylene-co-hexafluoropropene) (PTFE-HFP), poly(tetrafluoroethylene-co-vinyl alcohol) (PTFE-VAL), poly(tetrafluoroethylene-co-vinyl acetate) (PTFE-VAC), poly(tetrafluoroethylene-co-propene) (PTFEP) poly(hexafluoropropene-co-vinyl alcohol) (PHFP-VAL), poly(ethylene-co-tetrafluoroethylene) (PETFE), poly (ethylene-co-hexafluoropropene) (PEHFP), poly(vinylidene fluoride-co-chlorotrifluoroe-thylene) (PVDF-CTFE), and combinations thereof, and additional polymers and copolymers described in U.S. Publication 2004/0063805, incorporated by reference herein in its entirety for all purposes. Additional polyfluorocopolymers include tetrafluoroethylene (TFE)/perfluoroalkylvinylether (PAVE). PAVE can be perfluoromethylvinyl ether (PMVE), perfluoroethylvinylether (PEVE), or perfluoropropylvinylether (PPVE), as described in U.S. Publication 2006/0198866 and U.S. Pat. No. 7,049,380, both of which are incorporated by reference herein for all purposes in their entireties. Other polymers and copolymers include, polylactide, polycaprolacton-glycolide, polyorthoesters, polyanhydrides; poly-aminoacids; polysaccharides; polyphosphazenes; poly(ether-ester) copolymers, e.g., PEO-PLLA, or blends thereof, polydimethyl-siolxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters and any polymer and copolymers described in U.S. Publication 2004/0063805, incorporated by reference herein in its entity.

The graft components, as discussed herein, may be attached to the self-expanding stent elements by using a coupling member that is generally a flat ribbon or tape having at least one generally flat surface. In certain instances, the tape member is made from expanded PTFE (ePTFE) coated with an adhesive. The adhesive may be a thermoplastic adhesive. In certain instances, the thermoplastic adhesive may be fluorinated ethylene propylene (FEP). More specifically, an FEP-coated side of the ePTFE may face toward and contacts an exterior surface of the self-expanding stent and graft component, thus attaching the self-expanding stent to the graft component. Materials and method of attaching a stent to the graft is discussed in U.S. Pat. No. 6,042,602 to Martin, incorporated by reference herein for all purposes.

The stent component(s) discussed herein can be fabricated from a variety of biocompatible materials. These materials may include 316L stainless steel, cobalt-chromium-nickel-molybdenum-iron alloy ("cobalt-chromium"), other cobalt alloys such as L605, tantalum, Nitinol, or other biocompatible metals. In certain instances, as discussed in detail above, the stent (and graft) may be self-expanding. In other instances, the prosthesis may be balloon expandable.

The stent component(s) discussed herein may be constructed from a reasonably high strength material, i.e., one which is resistant to plastic deformation when stressed. In one embodiment, the stent component(s) comprise a wire which is helically wound around a mandrel having pins arranged thereon so that the helical turns and undulations can be formed simultaneously. Other constructions may also be used. In certain instances, the stent component(s) are made from a super-elastic alloy. There are a variety of disclosures in which super-elastic alloys such as nitinol are used in stents. See for example, U.S. Pat. No. 4,503,569, to Dotter; U.S. Pat. No. 4,512,338, to Balko et al.; U.S. Pat. No. 4,990,155, to Wilkoff; U.S. Pat. No. 5,037,427, to Harada, et al.; U.S. Pat. No. 5,147,370, to MacNamara et al.; U.S. Pat. No. 5,211,658, to Clouse; and U.S. Pat. No. 5,221,261, to Term in et al.

A variety of materials variously metallic, super elastic alloys, such as Nitinol, are suitable for use in the stent component(s). Primary requirements of the materials are that they be suitably springy even when fashioned into very thin sheets or small diameter wires. Various stainless steels which have been physically, chemically, and otherwise treated to produce high springiness are suitable as are other metal alloys such as cobalt chrome alloys (e.g., ELGILOY®), platinum/tungsten alloys, and especially the nickel-titanium alloys generically known as "nitinol".

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

What is claimed is:

1. A delivery system comprising:
   a catheter having a leading end and a trailing end;
   an expandable device arranged near the leading end of the catheter and including a proximal end, a distal end, and a flow lumen extending therebetween;
   an actuation wire coupled to the expandable device at one or more locations thereon, the actuation wire being configured to bidirectionally steer the expandable device proximally and distally during delivery thereof; and
   at least one tether arranged through a portion of the expandable device, arranged through the actuation wire and configured to couple the actuation wire to the expandable device, wherein the at least one tether is configured to uncouple and release from the expandable device in response to tension applied to the actuation wire after delivery of the expandable device.

2. The delivery system of claim 1, wherein the expandable device is configured to deploy at a tortious vessel having a curvature with at least one inflection point, and the actuation wire is configured to maintain the proximal end of the expandable device approximately perpendicular to the inflection point in the curvature of the tortious vessel during delivery of the expandable device.

3. The delivery system of claim 1, wherein the actuation wire is coupled to the expandable device adjacent the proximal end via the at least one tether being arranged through the actuation wire and the portion of the expandable device.

4. The delivery system of claim 1, wherein the actuation wire is configured to bidirectionally steer the expandable device proximally and distally during delivery thereof.

5. The delivery system of claim 1, wherein the at least one tether includes two tethers, and the actuation wire is coupled to the expandable device at two or more locations via the two tethers.

6. The delivery system of claim 5, wherein the actuation wire includes a bifurcation including a first branch and a second branch, and the first branch and the second branch are coupled to the expandable device at the two or more locations via a first of the two tethers being arranged through the first branch, and a second of the two tethers being arranged through the second branch.

7. The delivery system of claim 1, wherein the at least one tether is arranged through the actuation wire and arranged through the expandable device at two locations to couple the actuation wire to the expandable device.

8. The delivery system of claim 7, wherein the at least one tether extends from and through the actuation wire and through the expandable device at the two locations adjacent the proximal end of the expandable device.

9. The delivery system of claim 7, wherein the at least one tether includes two tethers, and the two tethers extend from and through the actuation wire and through the expandable device at the two locations adjacent the proximal end of the expandable device.

10. The delivery system of claim 1, wherein the at least one tether comprises a bio-absorbable material.

11. The delivery system of claim 1, wherein one of the proximal end and the distal end of the expandable device is operable to be maintained parallel to a target location and another of the proximal end and the distal end of the expandable device is operable to be bidirectionally steered by the actuation wire.

12. A delivery system comprising:
    a catheter having a leading end and a trailing end;
    an expandable device arranged near the leading end of the catheter and including a proximal end, a distal end, and a flow lumen extending therebetween;
    an actuation wire coupled to the expandable device at two or more locations thereon, the actuation wire being configured to bi-directionally steer the expandable device during delivery thereof such that one of the proximal end and distal end angulate s to a target location; and
    at least one tether configured to couple the actuation wire to the expandable device to uncouple and release from the expandable device in response to tension applied to the actuation wire after delivery of the expandable device.

13. The delivery system of claim 12, wherein the actuation wire bifurcates to form a first branch and a second branch to form a y-shaped structure, and the first branch and the second branch are coupled to the expandable device at two locations.

14. The delivery system of claim 13, further comprising two tethers configured to couple the actuation wire to the two or more locations on the expandable device.

15. The delivery system of claim 14, wherein a first of the two tethers being arranged through a proximal end of the first branch and through the expandable device, and a second of the two tethers being arranged through a proximal end of the second branch and through the expandable device to couple the actuation wire to the two or more locations on the expandable device.

16. The delivery system of claim 15, wherein the at least one tether and the actuation wire form a y-shaped structure.

17. The delivery system of claim 12, further comprising at least one tether arranged through the actuation wire and arranged through the expandable device at two locations to couple the actuation wire to the expandable device.

* * * * *